(12) United States Patent
DeAnglis et al.

(10) Patent No.: US 8,900,822 B2
(45) Date of Patent: Dec. 2, 2014

(54) FIBRINOGEN ASSAY

(75) Inventors: Ashley DeAnglis, Skillman, NJ (US); Elif Burcoglu, New Brunswick, NJ (US)

(73) Assignee: Ethicon, Inc., Somerville, NJ (US)

( * ) Notice: Subject to any disclaimer, the term of this patent is extended or adjusted under 35 U.S.C. 154(b) by 574 days.

(21) Appl. No.: 13/300,795

(22) Filed: Nov. 21, 2011

(65) Prior Publication Data
US 2013/0130282 A1    May 23, 2013

(51) Int. Cl.
*G01N 33/53* (2006.01)
*G01N 31/00* (2006.01)
*G01N 33/86* (2006.01)

(52) U.S. Cl.
CPC ..................................... *G01N 33/86* (2013.01)
USPC ........... 435/7.21; 435/7.1; 436/501; 436/518; 530/300; 530/350; 424/9.1; 424/130.1

(58) Field of Classification Search
None
See application file for complete search history.

(56) References Cited

U.S. PATENT DOCUMENTS

| | | | |
|---|---|---|---|
| 4,438,209 | A | 3/1984 | Mosier |
| 5,817,768 | A | 10/1998 | Grieninger et al. |
| 5,821,068 | A | 10/1998 | Soe et al. |
| 5,876,947 | A | 3/1999 | Kudryk et al. |
| 6,074,837 | A | 6/2000 | Procyk et al. |
| 7,666,803 | B2 | 2/2010 | Shetty et al. |
| 7,790,410 | B2 | 9/2010 | Yu et al. |
| 2002/0132370 | A1 | 9/2002 | Lassen et al. |
| 2005/0202527 | A1 | 9/2005 | Le Bonniec et al. |
| 2006/0088589 | A1 | 4/2006 | Gorman et al. |
| 2009/0246238 | A1 | 10/2009 | Gorman et al. |
| 2011/0053193 | A1 | 3/2011 | Deanglis et al. |

FOREIGN PATENT DOCUMENTS

| | | |
|---|---|---|
| EP | 0345811 | 8/1994 |
| WO | WO 2007/030531 | 3/2007 |
| WO | WO 2007/030571 | 3/2007 |

OTHER PUBLICATIONS

Santa Cruz Biotechnology, Inc., Fibrinogen Antibody (1F7): sc-51892, (2010). [Retrieved from the internet on Jan. 14, 2012 <url:http://www.scbt.com/datasheet-51892-fibrinogen-alpha-1f7-antibody.html>].
Chen et al., Quantitative Organellar Proteomics Analysis of Rough Endoplasmic Reticulum from Normal and Acute Pancreatitis Rat Pancreas, J. Proteome Res. 2010, pp. 885-896, vol. 9, No. 2.
Amiral, J. et al., "Monoclonal antibodies to different neo-epitopes on fibrinogen and fibrin degradation products" Blood Coagul Fibrinolysis. (1990) vol. 1, Issue 4-5 pp. 447-52. (Abstract).
DeAnglis, A.P. et al, "Fibrin(ogen) and Inflammation: Current Understanding and New Perspectives" Clinical Immunology Newsletter (1999) vol. 19 No. 8/9 pp. 111-118.
Fareed, J. et al., "Useful laboratory tests for studying thrombogenesis in acute cardiac syndromes" Clinical Chemistry (1998) vol. 44, Issue 8(B) pp. 1845-1853.
Gorkun, O.V. et al., "The conversion of fibrinogen to fibrin: recombinant fibrinogen typifies plasma fibrinogen" Blood (1997) vol. 89, No. 12 pp. 4407-4414.
Hoegee-de, Nobel et al.,"A monoclonal antibody-based quantitative enzyme immunoassay for the determination of plasma fibrinogen concentrations" Thromb Haemost. (1988) vol. 60 Issue 3 pp. 415-418. (Abstract).
Koppert et al., "A monoclonal antibody, specific for human fibrinogen, fibrinopeptide A-containing fragments and not reacting with free fibrinopeptide A" Blood (1985) vol. 66, No. 3 pp. 503-507.
Marecek, F. et al., "Comparison of several mouse and rat monoclonal antibodies against human fibrinogen" Hybridoma. (1996) vol. 15, No. 6 pp. 423-7.
Pfitzner, SA et al., "Fibrin detected in plasma of patients with disseminated intravascular coagulation by fibrin-specific antibodies consists primarily of high molecular weight factor XIIIa-crosslinked and plasmin-modified complexes partially containing fibrinopeptide A" Thrombosis & Haemostasis (1997) vol. 78 Issue 3 pp. 1069-1078. (Abstract).
Shainoff, J.R. et al., "Isolation and characterization of the fibrin intermediate arising from cleavage of one fibrinopeptide A from fibrinogen" Journal of Biological Chemistry (1996) vol. 271, No. 39 pp. 24129-24137.

*Primary Examiner* — Lisa Cook

(74) *Attorney, Agent, or Firm* — David R. Crichton; Leo B. Kriksunov

(57) ABSTRACT

The present invention is directed to a method of detecting intact fibrinogen, comprising the steps of: a) providing a sample containing at least some fibrinogen optionally converted at least in part to fibrin, and optionally containing thrombin; b) solubilizing the sample in a solubilizing solution that inhibits thrombin activity; c) after optional SDS-PAGE transferring/applying a portion of said sample to a protein-binding membrane; d) reacting the fibrinogen with a primary monoclonal antibody capable of binding to fibrinopeptide A moiety; and e) detecting the quantity of intact fibrinogen in the sample by quantifying the amount of the bound primary monoclonal antibody.

9 Claims, 7 Drawing Sheets

FIGURE 5

FIBRINOGEN ASSAY

FIELD OF THE INVENTION

The present invention relates generally to an immunoassay for detecting fibrinogen in the presence of thrombin.

BACKGROUND

Blood is a liquid tissue that includes red cells, white cells, corpuscles, and platelets dispersed in a liquid phase. The liquid phase is plasma, which includes acids, lipids, dissolved electrolytes, and proteins. One particular protein present in the liquid phase is fibrinogen. When bleeding occurs, fibrinogen reacts with thrombin (an enzyme) to form an insoluble fibrin clot.

In a wide variety of circumstances, animals, including humans, can suffer from bleeding due to wounds or during surgical procedures. In some circumstances, the bleeding is relatively minor, and normal blood clotting functions in addition to the application of simple first aid are all that is required. In other circumstances substantial bleeding can occur. These situations usually require specialized equipment and materials as well as personnel trained to administer appropriate aid.

In an effort to address the above-described problems, materials have been developed for controlling excessive bleeding. Topical Absorbable Hemostats (TAHs) are widely used in surgical applications. TAHs encompass products based on various woven or non-woven fabrics or sponges, typically made of at least partially resorbable materials, ranging from natural to synthetic polymers and combinations thereof, including lactide-glycolide based co-polymers such as polyglactin 910, oxidized cellulose, oxidized regenerated cellulose (ORC), gelatin, collagen, chitin, chitosan, etc. To improve the hemostatic performance, scaffolds based on the above materials can be combined with biologically-derived clotting factors, such as thrombin and/or fibrinogen.

A number of hemostatic formulations currently available on the market or in development utilize lyophilized fibrinogen, frequently in combination with lyophilized thrombin, with hemostatic formulations applied in the form of dry powder, semi-liquid paste, liquid formulation, or optionally disposed on a supporting scaffold such as absorbable fabric scaffold.

A number of prior art references are directed to blood plasma analysis for fibrin or fibrinogen and related assays, development of monoclonal antibodies (mABs), and mABs directed against fibrinogen degradation products. These prior art references teach assays whereby no thrombin (or only the inactive precursor prothrombin) is present in the sample; are not applicable to dry lyophilized proteins of interest; have no solubilization steps and/or thrombin inactivation steps.

An article entitled "Useful laboratory tests for studying thrombogenesis in acute cardiac syndromes", Fareed et al., Clinical Chemistry. 44(8 Pt 2):1845-53, 1998, discloses utilizing antibodies to fibrinopeptide A (FpA) in ELISA and radioimmunoassay methods for clinical applications, which is a common use for antibodies against FpA as a marker for thrombosis (intravascular blood clots).

An article entitled "Fibrin detected in plasma of patients with disseminated intravascular coagulation by fibrin-specific antibodies consists primarily of high molecular weight factor XIIIa-crosslinked and plasmin-modified complexes partially containing fibrinopeptide A", Pfitzner et al., Thrombosis & Haemostasis. 78(3):1069-78, 1997, discloses that plasma samples from patients with active clotting were evaluated with various antibodies (including antibody to fibrinopeptide A) to characterize the fibrinogen/fibrin in clot complexes. The starting sample material was plasma.

An article entitled "The conversion of fibrinogen to fibrin: recombinant fibrinogen typifies plasma fibrinogen", Gorkun et al., Blood. 89(12):4407-14, 1997, discloses that HPLC was used to quantify the amount of FpA released from the two forms of fibrinogen. The starting sample material was liquid (plasma).

An article entitled "Isolation and characterization of the fibrin intermediate arising from cleavage of one fibrinopeptide A from fibrinogen" Shainoff et al., Journal of Biological Chemistry. 271(39):24129-37, 1996, discloses a study of "alpha-profibrin" (fibrin monomer with a single fibrinopeptide A released, rather than the usual two FpA peptides released) and its ability to polymerize. A monoclonal antibody that was directed against FpA was used to determine if FpA had been cleaved. The starting material was a solution containing fibrinogen, fibrin or intermediates.

An article entitled "A monoclonal antibody, specific for human fibrinogen, fibrinopeptide A-containing fragments and not reacting with free fibrinopeptide" Koppert et al., Blood. 66(3):503-7, 1985, describes the production of a monoclonal antibody to FpA.

An article entitled "Monoclonal antibodies to different neo-epitopes on fibrinogen and fibrin degradation products", Amiral et al., Blood Coagul Fibrinolysis. 1990 October; 1(4-5):447-52, discloses an attempt to develop various monoclonal antibodies specific for the neo-epitopes unmasked during the degradation of fibrin or fibrinogen that are classified in three reactivity classes: D and D-dimer, D-dimer and early fibrinogen, and fibrin degradation products. These monoclonal antibodies were used to develop latex slide assays and ELISA techniques. Two types of citrated plasma assays were obtained; those which were specific for fibrin-related products and those evaluating the totality of fibrin or fibrinogen degradation products.

An article entitled "A monoclonal antibody-based quantitative enzyme immunoassay for the determination of plasma fibrinogen concentrations", Hoegee-de Nobel et al., Thromb Haemost. 1988 Dec. 22; 60(3):415-8, discloses monoclonal antibody-based quantitative enzyme immunoassay for the determination of plasma fibrinogen concentrations and teaches that immunological assays for fibrinogen fibrinopeptide A, which do not detect degradation products of fibrinogen.

An article entitled "Comparison of several mouse and rat monoclonal antibodies against human fibrinogen", Marecek et al., Hybridoma. 1996 December; 15(6):423-7, discloses that six monoclonal antibodies raised against human fibrinogen have been characterized. Mouse monoclonal antibodies were targeted against sequential epitopes on the immunodominant D-domain of fibrinogen and they crossreacted with all molecules containing the D-domain [fibrin, fibrin (ogen)-degradation products].

U.S. Pat. No. 7,790,410 B2 discloses a method of screening a candidate material for hemocompatibility comprising: (1) contacting a candidate material with fibrinogen; (2) contacting the candidate material from step (1) with thrombin; determining a presence or level of a fibrinogen cleavage product from step (2); and determining if the candidate material is hemocompatible based on the presence or level of the fibrinogen cleavage product.

U.S. Pat. No. 6,074,837 discloses a competitive immunoassay for determining fibrin and fibrin degradation products in a sample, said immunoassay comprising individually contacting said sample and a positive control of known fibrin and fibrin degradation products concentration with a labeled antibody which specifically binds to said fibrin and fibrin degradation products, and after a suitable incubation period, separating bound labeled antibody from unbound labeled antibody, measuring bound label, and comparing measured bound label in the contacted sample to measured bound label in the contacted positive control to determine the presence or amount of said fibrin and fibrin degradation products in said sample, wherein the improvement comprises using a modified fibrinogen as said fibrin and fibrin degradation products in said positive control. The reference further discloses a sandwich immunoassay for determining fibrin and fibrin degradation products in a sample, said immunoassay comprising coating wells of a microtiter plate with a first antibody which specifically binds to said fibrin, said fibrin degradation products and fibrin monomer; contacting said sample and a positive control of known fibrin or fibrin monomer concentration to separate wells of said microtiter plate; removing any unbound sample or positive control from its respective well; contacting each well with a labeled anti-first antibody antibody; measuring any bound label in each well and comparing the measured bound label in the sample wells to the measured bound label in the positive control wells to determine the presence or amount of said fibrin and fibrin degradation products in the sample, wherein the improvement comprises using a modified fibrinogen as said fibrin or fibrin monomer in said positive control, the modified fibrinogen obtained by a process comprising the following steps: (1) partially reducing 3 to 25 micromolar fibrinogen with 0.25 millimole per nanomole of said fibrinogen with a reducing agent at 30-40° C. under non-denaturing conditions in the absence of divalent cations for 0.5 to 1.5 hours, then (2) blocking thiol groups of any free cysteines formed during step (1) by reacting the product of step (1) with a blocking agent that does not cause precipitation of the product of step (2), then (3) reacting the product of step (2) with a clotting enzyme in a physiological buffer in the absence of divalent cations to release fibrinopeptides A and B, and (4) terminating the activity of said clotting enzyme.

U.S. Pat. No. 5,876,947 discloses a continuous cell line, identified as P10 and deposited as ATCC Accession No. HB-12398 that produces a monoclonal antibody that binds specifically with an epitope defined by a specific amino acid sequence and further discloses a monospecific antibody or fragment thereof that binds specifically to the epitope as present in fibrinogen, fibrinopeptide B, or des-Arg fibrinopeptide B.

U.S. Pat. No. 4,438,209 discloses a competitive radioimmunoassay method for determining the concentration of fibrinopeptide A in plasma wherein first, a sample of blood is collected, the thrombin in said sample is inhibited by an inhibiting amount of a thrombin inhibitor and plasma is separated from said sample, and second, a sample of said plasma is contacted under radioimmunoassay competitive binding conditions with a sufficient amount of an antibody to fibrinopeptide A and radioactively labeled fibrinopeptide A, thereafter, antibody bound fibrinopeptide A is separated from the unbound fibrinopeptide A and radioactivity measured, the improvement comprising using as the inhibitor for thrombin an inhibitor selected from the group consisting of D-phenylalanyl-L-propyl-L-N-[2(1-chloro-7-guanidoheptane-2-one)] the hydrochloric acid addition salt thereof; the hydrofluoric acid addition salt thereof, the acetic acid addition salt thereof and the citric acid addition salt thereof.

European Patent publication EP 345,811 A2 discloses a hybridoma which secretes a monoclonal antibody specific for human fibrinopeptide A, but which does not react with either intact fibrinogen or human fibrinopeptide A-containing fibrinogen fragments. The reference further discloses a method for determining free FpA comprising (a) immobilizing a monoclonal antibody, said monoclonal antibody being according to claim 1, (b) contacting the immobilized monoclonal antibody from (a) with labeled hFPA peptide or a labeled fragment thereof or a Tyr derivative thereof, and a plasma sample, and (c) assaying for the label.

U.S. Pat. No. 5,817,768 discloses a monospecific antibody, which binds with an epitope of the $\alpha_E$ subunit of fibrinogen, wherein said monospecific antibody is produced by a hydridoma cell line selected from the group consisting of hybridoma cell line identified as #3-10, hybridoma cell line identified as #29-1, and hybridoma cell line #148-B.

PCT patent publication WO2007/030571 A2 discloses identification of disease target molecules and the development of imaging reagents and diagnostic assays specific to those molecules. Described therein are methods and reagents for the identification of molecular targets specific to a disease or disease state, methods of imaging technology which can be used, the development of specific molecular imaging reagents, clinical validation of the imaging reagents, and clinical indications for molecular imaging. The reference claims a target-specific imaging reagent, comprising an affinity agent coupled to an imaging agent, wherein said affinity agent specifically binds to a biological molecule, wherein expression of said biological molecule is predictive of a disease or a disease state.

PCT patent publication WO 2007/030531 describes both the identification of disease target molecules and the development of imaging reagents and diagnostic assays specific to those molecules. Described therein are methods and reagents for the identification of molecular targets specific to a disease or disease state, methods of imaging technology which can be used, the development of specific molecular imaging reagents, clinical validation of the imaging reagents, and clinical indications for molecular imaging. The reference claims a target-specific imaging reagent, comprising an antibody coupled to an imaging agent detectable by magnetic resonance, wherein said antibody specifically binds to Glypican-3, wherein expression of Glypican-3 is predictive of liver cancer.

U.S. Patent application publication No. 20110053193 discloses a method for determining the activity or functionality of either a first reactive component or a second reactive component in an unreacted admixture of the first reactive component and the second reactive component, comprising the steps of (a) reversibly inhibiting the first reactive component to yield a mixture having an inactivated first reactive component and the second reactive component; (b) adding to the mixture a known amount of the second reactive component when evaluating the activity of the first reactive component, or a known amount of the first reactive component when evaluating the activity of the second reactive component; (c) reversibly activating the first reactive component; (d) allowing the first reactive component to react with the second reactive component originally present in the admixture and the known amount of the second reactive component, or allowing the first reactive component to react with the second reactive component originally present in the admixture and the known amount of the first reactive component; and (e) determining the activity or functionality of first or second reactive component originally present in the admixture.

Hemostatic patches or pads containing lyophilized thrombin and fibrinogen, optionally on absorbable scaffolds, lack an assay to quantify the activation status of the biological components (i.e. whether fibrinogen has been converted to fibrin). Because fibrinogen and thrombin spontaneously react upon hydration, exposure of the hemostatic pad to moisture could cause premature activation (prior to application to the bleeding site) of the biological components and could potentially impact the pad's overall stability and performance. Currently fibrin sealant delivery devices, deploying a mixture of fibrinogen and thrombin solutions on a wound for hemostatic or tissue sealing applications lack a test capable of directly evaluating fibrinogen to fibrin conversion. One objective of the Applicants' work was to develop a robust assay that measures both the rate and extent of the fibrinogen to fibrin conversion reaction as well as to measure the amount of intact fibrinogen in the presence of thrombin.

SUMMARY OF THE INVENTION

Briefly stated, the present invention is directed to a method of detecting intact fibrinogen, comprising the steps of: providing a sample containing at least some fibrinogen optionally converted at least in part to fibrin, and optionally containing thrombin; solubilizing the sample in a solubilizing solution and inhibiting thrombin activity; after optional SDS-PAGE transferring a portion of said sample onto a protein-binding membrane; reacting the fibrinogen with a primary monoclonal antibody capable of binding to fibrinopeptide A moiety; and detecting the quantity of intact fibrinogen in the sample by quantifying the amount of the bound primary monoclonal antibody.

In one embodiment, the present invention is directed to a method of detecting intact fibrinogen, comprising the steps of: Providing a sample containing at least some fibrinogen optionally converted at least in part to fibrin, and optionally containing thrombin; Solubilizing the sample in a solubilizing solution that inhibits thrombin activity; Transferring a portion of said sample to a gel and subjecting said portion to electrophoresis; Transferring a fraction of said portion of the sample from said gel to a protein-binding membrane and immobilizing the fibrinogen on said membrane; Subjecting said membrane to at least one blocking step; Reacting the fibrinogen immobilized on said membrane with a primary monoclonal antibody capable of binding to fibrinopeptide A moiety to form a fibrinogen-antibody complex; Subjecting said membrane to at least one washing step to remove any unbound primary monoclonal antibody; Reacting said monoclonal antibody that formed the fibrinogen-antibody complex with a secondary antibody having a marker; Subjecting said membrane to at least one washing step to remove any unbound secondary antibody having a marker; and Detecting the quantity of intact fibrinogen in the sample by quantifying the amount of the marker.

In an alternative embodiment, the fibrinogen immobilized on said membrane is reacted with a primary monoclonal antibody capable of binding to fibrinopeptide B moiety to form a fibrinogen-antibody complex.

The sample can contain an unknown amount of intact fibrinogen. The sample can be solid, liquid, or semi-liquid. The sample can contain lyophilized fibrinogen and thrombin.

The method can utilize SDS-PAGE and/or Western blot or dot blot. The primary monoclonal antibody capable of binding to fibrinopeptide A moiety can be clone 1F7. In an alternative embodiment, the primary monoclonal antibody is capable of binding to fibrinopeptide B moiety. Fibrinopeptides A and B are cleaved by the enzymatic action of thrombin from the amino-termini of the Aα and Bβ chains of fibrinogen, respectively. These peptides consist of 16 and 14 amino acids, which have molecular weights of 1536.6 Da and 1570.6 Da, respectively. The secondary antibody having a marker is goat anti-mouse IgG, conjugated to alkaline phosphatase.

The step of detecting the quantity of intact fibrinogen in the sample by quantifying the amount of the marker can be performed by incubating the protein-binding membrane with a substrate for alkaline phosphatase.

The marker can be an electrochemically detectable marker, a colorimetrically detectable marker, radiologically detectable marker, magnetically detectable marker or a fluorescent marker.

In another embodiment, the present invention is directed to a method for assessing the performance or stability of a hemostatic device containing at least one biologic component that is fibrinogen comprising comparing the quantity of intact fibrinogen in a sample obtained according to the method described above relative to a threshold level of intact fibrinogen.

In another embodiment, the present invention is directed to a method of detecting intact fibrinogen, comprising the steps of: Providing a sample containing at least some fibrinogen optionally converted at least in part to fibrin, and optionally containing thrombin; Solubilizing the sample in a solubilizing solution that inhibits thrombin activity; Applying a portion of said sample to a protein-binding membrane and immobilizing the fibrinogen on said membrane; Subjecting said membrane to at least one blocking step and removing fibrinopeptide A cleaved from fibrinogen from dot blot assay membrane; Reacting the fibrinogen immobilized on said membrane with a primary monoclonal antibody capable of binding to fibrinopeptide A moiety to form a fibrinogen-antibody complex; Subjecting said membrane to at least one washing step to remove any unbound primary monoclonal antibody; Reacting said monoclonal antibody that formed the fibrinogen-antibody complex with a secondary antibody having a marker; Subjecting said membrane to at least one washing step to remove any unbound secondary antibody having a marker; and Detecting the quantity of intact fibrinogen in the sample by quantifying the amount of the marker.

In another embodiment, the present invention is directed to a method of detecting intact fibrinogen, comprising the steps of: Providing a sample containing at least some fibrinogen optionally converted at least in part to fibrin and optionally containing thrombin; Solubilizing the sample in a solubilizing solution that inhibits thrombin activity; Transferring a portion of said sample to a protein-binding membrane and immobilizing the fibrinogen on said membrane; Subjecting said membrane to at least one washing and one blocking step and removing fibrinopeptide A cleaved from fibrinogen from dot blot assay membrane; Reacting the fibrinogen immobilized on said membrane with a primary monoclonal antibody capable of binding to fibrinopeptide A moiety to form a fibrinogen-antibody complex; and Detecting the quantity of intact fibrinogen in the sample by quantifying the amount of the primary monoclonal antibody forming the fibrinogen-antibody complex bound.

BRIEF DESCRIPTION OF FIGURES

FIG. 5 shows an image of the nitrocellulose membrane after performing the dot blot assay.

DETAILED DESCRIPTION OF THE INVENTION

Figure 1:
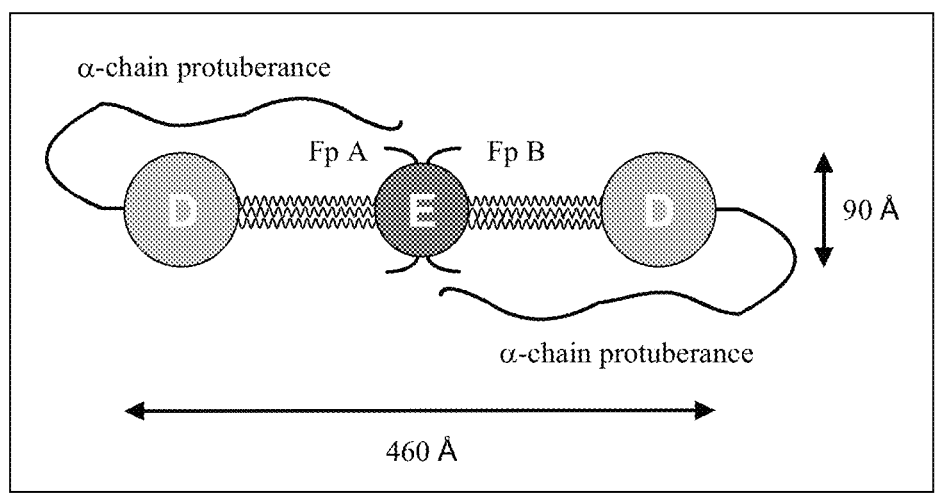
FIG. 1 schematically shows the structure of fibrinogen.

Fibrinogen is the precursor protein of the blood clot matrix. It has a molecular weight of 340,000 Da and consists of 3 pairs of non-identical polypeptide chains, Aα, Bβ, and γ, linked together by disulfide bonds. Fibrinogen has a trinodular structure: two identical D terminal globular domains and a central E globular domain. All of these domains are connected by supercoiled α-helices, as schematically shown in FIG. 1, where designations FpA and FpB correspond to fibrinopeptides A and B respectively.

Under normal circumstances, blood is contained within a continuous network of conduits lined by endothelial cells. The luminal surface of the endothelial cells forms a "hemocompatible" barrier that inhibits the spontaneous coagulation of blood and the adhesion of platelets. When the endothelial lining becomes disrupted, however, a series of biochemical reactions are initiated to stop blood loss. Immediately after vascular injury, an injured vessel constricts so that blood will be diverted from the site of injury. The process of coagulation is initiated by the binding of specific plasma proteins and platelets to newly exposed subendothelial structures resulting from the disruption of the endothelial lining. Damaged endothelial cells also start the process of coagulation by releasing tissue factor, a complex of protein and phospholipid. Once coagulation has been initiated, a "cascade" of enzyme activations occurs resulting in the formation of a platelet-rich blood clot, or hemostatic "plug" at the site of injury.

A reference is made to the following publication, which is incorporated herein in its entirety by reference, A P DeAnglis and G S Retzinger, "Fibrin(ogen) and Inflammation: Current Understanding and New Perspectives", Clinical Immunology Newsletter (1999) 18, 111-118.

Figure 2:
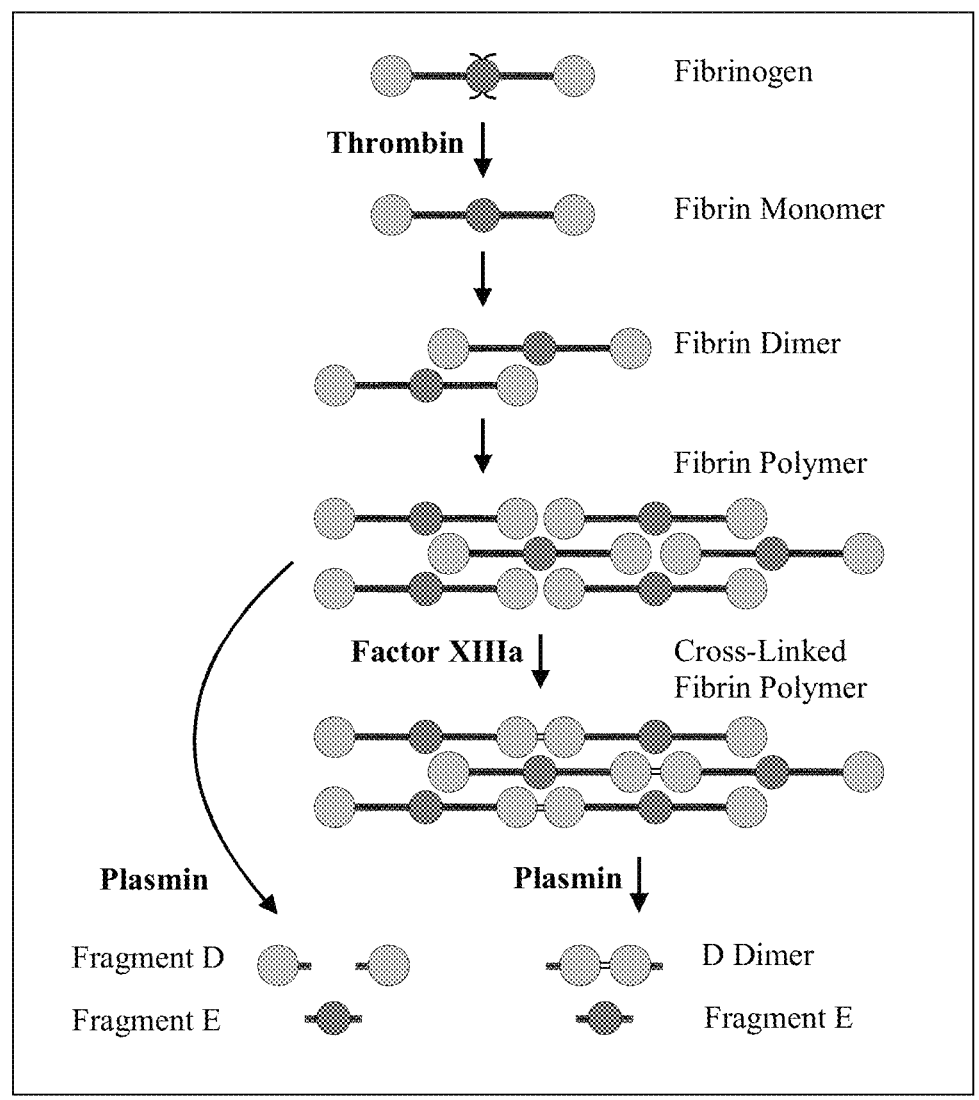
FIG. 2 schematically shows fibrinogen conversion to fibrin.

A critical step in the formation of a blood clot is thrombin-catalyzed conversion of fibrinogen to fibrin. For this conversion to occur, thrombin itself must be converted from its inactive precursor, prothrombin, by an enzyme complex generated during the coagulation process. Thrombin, a serine protease, hydrolyzes specific arginine-glycine bonds located at the amino termini of the Aα and Bβ polypeptide chains of fibrinogen, releasing from the protein two pairs of negatively charged protein fragments termed fibrinopeptides A and B. These peptides constitute only 2% of the overall mass of fibrinogen. The release of the fibrinopeptides changes the charge within the E domain from negative to positive, facilitating interactions of that domain with the negatively charged D domains of other fibrin molecules. The interactions of fibrin monomers with each other result in the spontaneous assembly of fibrin monomers in a half-staggered arrangement, as schematically shown in FIG. 2. The specific association of fibrin monomers that occurs during fibrin polymerization is a result of non-covalent interactions between complementary polymerization sites, termed knobs and holes, in the E and D domains of fibrin monomers. Initially, fibrin polymer assembly produces a protofibril, a long fibrin oligomer having the thickness of two molecules. In time, protofibrils associate laterally to form groups of protofibrils, which subsequently aggregate into larger fibrin fibers. The process of protofibril assembly results in the formation of an interconnected network of fibrin fibers in the characteristic half-staggered array.

The conversion of fibrinogen to fibrin is a critical step in the process of hemostasis involving the thrombin catalyzed cleavage of fibrinopeptides A and B from fibrinogen, resulting in the formation of fibrin monomer, which is subsequently assembled into fibrin polymer. Measuring the extent of fibrinogen to fibrin conversion in the presence of thrombin is challenging, since the enzyme will spontaneously hydrolyze fibrinogen to fibrin under typical conditions. The amount of fibrinogen can be measured only if the protein is solubilized. If the proteins are sufficiently solubilized, thrombin will spontaneously convert fibrinogen to fibrin preventing the measurement of the original fibrinogen.

Objectives

The objective of the present invention is to provide a method that can measure the amount of fibrinogen to fibrin conversion in a starting material consisting of dry fibrinogen and/or fibrin, hereafter referred to as fibrinogen/fibrin, and thrombin powders.

An additional objective of the present invention is to provide a method that allows the measurement of potential premature conversion of fibrinogen to fibrin of a starting material consisting of dry fibrinogen/fibrin and thrombin powders. Spontaneous fibrin formation is prevented by inhibiting thrombin during solubilization.

An additional objective of the present invention is to provide a method that can be used to assess the rate and extent of reaction between fibrinogen and thrombin in liquid formulations containing the two proteins.

A still further objective of the present invention is to provide a method that can be used to assess the biochemical reaction between fibrinogen and thrombin to optimize liquid formulations or mixing efficiency (applicable to liquid fibrin sealant formulations and specialized mixing tips).

A still further objective of the present invention is to provide a method that utilizes solubilization of the proteins for measuring the amount of fibrinogen and fibrin. To prevent spontaneous fibrin formation during sample preparation, optimized conditions which inactivate thrombin immediately on hydration are used to solubilize the proteins. The sample preparation procedure must prevent/minimize any fibrin generation, so that the amount of fibrinogen in the original sample can be determined.

A further objective of the present invention is to provide a method that can have diagnostic and clinical applications to identify the presence of fibrinogen and differentiate between fibrinogen and fibrin when the two proteins are present together. The deposition of fibrinogen and fibrin are important markers for many disease states, eg, inflammation, atherosclerosis, tumors, thromboemboli, etc. The presence and/or relative amounts of fibrinogen and fibrin can be used as diagnostic or prognostic indicators.

Method Overview

According to an embodiment of the present invention, lyophilized fibrinogen and thrombin are solubilized prior to or as a part of the inventive intact fibrinogen assay. To avoid fibrinogen to fibrin conversion during solubilization, thrombin must be inactivated immediately upon hydration. To measure the amount of fibrinogen, the mixture of proteins can be separated by sodium dodecyl sulfate polyacrylamide gel electrophoresis (SDS-PAGE) and blotted onto a protein-binding membrane (e.g. nitrocellulose, polyvinylidene fluoride). Alternatively, the mixture of proteins can be applied directly onto the membrane. Using an antibody directed against FpA or FpB, intact fibrinogen can be detected on the membrane, however, if the original intact fibrinogen has been converted to fibrin (through fibrinopeptide cleavage from fibrinogen), no protein will be detected on the membrane. This inventive method is capable of assessing the conversion of fibrinogen to fibrin, and is applicable to any mixture of fibrinogen/fibrin and thrombin.

Additionally, the protein solubilization step, required for the measurement of fibrinogen, can result in a spontaneous reaction between fibrinogen and thrombin and thus preventing the accurate measurement of any reaction prior to sample solubilization. The inventors discovered that specific solubilization conditions inhibit thrombin activity while still solubilizing the proteins. The inventive solubilization reagents/conditions include a thrombin inhibitor, a high concentration of detergent and a reducing agent in combination with high temperature.

The analytical method to measure the conversion of fibrinogen to fibrin described in the present invention is an immunoblotting technique which utilizes an antibody specific for the portion of the fibrinogen molecule that is hydrolyzed and cleaved by the enzyme thrombin. Using this antibody, a sample containing fibrinogen is detected while a fully reacted sample containing only fibrin will not be detected by this antibody. A sample that is partially reacted will produce an intermediate response which can be quantified using the immunoblotting technique.

According to an embodiment of the present invention, a method of detecting (intact) fibrinogen comprises the solubilization step and the immunoblotting step.

The solubilization step entails solubilizing the sample while also inhibiting thrombin activity.

The immunoblotting step entails: transfer or application of samples onto a membrane; optional SDS-PAGE; blocking step; reacting the fibrinogen immobilized on membrane with a monoclonal primary antibody; washing step to remove unreacted primary antibody; reacting monoclonal antibody with a secondary antibody having a marker; washing step to remove unreacted secondary antibody; and detecting the quantity of intact fibrinogen by quantifying the amount of the marker.

Hemostatic Pad Containing Lyophilized Fibrinogen and Thrombin

A hemostatic pad containing lyophilized thrombin and fibrinogen on absorbable scaffold that was utilized in the experimental testing of the present invention is referred to herein as a fibrinogen-containing pad. The fibrinogen-containing pad consists of a composite structure including layers of Vicryl® (Polyglactin 910) and ORC (oxidized regenerated cellulose). The Vicryl® layer is coated with human fibrinogen and thrombin powders in a dry, unreacted state. When the product is applied onto a bleeding site, the proteins are hydrated which results in the conversion of fibrinogen to fibrin and formation of a fibrin clot. Fibrin formation on the tissue surface promotes hemostasis and adhesion to the tissue. It is critical that the proteins remain in an unreacted state prior to application to the tissue. Premature conversion of fibrinogen to fibrin (activation prior to use of the product) due to exposure to water during production or storage could have a negative impact on performance and stability.

U.S. Pat. No. 7,666,803 to Shetty, et al. entitled Reinforced absorbable multilayered fabric for use in medical devices is incorporated herein by reference in its entirety for all purposes and teaches a multilayered fabric comprising a first absorbable nonwoven fabric and a second absorbable woven or knitted fabric comprising oxidized polysaccharides.

Published United States Patent Application 2006/0088589 A1, entitled Method for making an absorbable hemostat, Gorman et al., is incorporated herein by reference in its entirety for all purposes, and discloses a method of making a wound dressing, characterized in that said method comprises: suspending thrombin and/or fibrinogen powder in a perfluorinated hydrocarbon carrier fluid in which they are not soluble, and applying the resulting suspension to a first absorbable nonwoven fabric.

Published United States Patent Application 2009/0246238A1 by Gorman et al., entitled "REINFORCED ABSORBABLE MULTILAYERED HEMOSTATIC WOUND DRESSING" is incorporated herein by reference in its entirety for all purposes and teaches a method for making a multilayered wound dressing having a first absorbable nonwoven fabric, one or more second absorbable woven or knitted fabric, thrombin and/or fibrinogen, comprising the steps of: (a) crimping absorbable polymer fibers or yarns in the range of about 10 to 30 crimps per inch; (b) cutting the crimped fibers or yarns to a staple length between about 0.1 and 2.5 inch; (c) carding the staple to form the first absorbable nonwoven fabric while controlling the humidity to about 20 to 60%, at a room temperature of about 15 to 24° C.; (d) attaching the first absorbable nonwoven fabric to the second absorbable woven or knitted fabric; (e) applying thrombin and/or fibrinogen to the first absorbable nonwoven fabric.

Fibrinogen-containing pads made as described in the above references were utilized in the experiments carried out in the practice of the present invention. The multi-layer matrix component of the fibrinogen-containing pad consists of a knitted ORC backing layer that is attached to a layer of Polyglactin 910 (PG910) non-woven fibers. During the manufacturing process, the PG910 fibers are carded into a batt and needle-punched to the ORC backing layer to produce the multi-layer matrix.

The biological components of the fibrinogen-containing pad are preferably lyophilized forms of the human fibrinogen and human thrombin. They respectively contain the biologically active ingredients, fibrinogen and thrombin, and other excipients. The compositions of the human fibrinogen and human thrombin as applied to the fibrinogen-containing pad are 2-20 mg/cm$^2$ fibrinogen and 1-150 IU/cm$^2$ thrombin.

In addition to measuring the degree of fibrinogen to fibrin conversion in a mixture of dry fibrinogen and thrombin, the present method can be used to measure the extent of fibrinogen to fibrin conversion in a liquid formulation containing fibrinogen and thrombin. Examples of such a formulation are commercially available fibrin sealants, composed of concentrated solutions of fibrinogen and thrombin which are applied simultaneously, but separately, to a bleeding site to control hemorrhage. When the two protein solutions are well mixed, fibrinogen is rapidly converted to fibrin. Measuring the rate and extent of fibrin formation is challenging due to the rapidity of fibrin formation and the insolubility of the resulting fibrin clot. Various approaches can be used to evaluate the degree of mixing of the liquids, however, these approaches do not assess biochemically the conversion of fibrinogen to fibrin. Using the immunoblotting techniques described here, the relative amounts of fibrinogen and fibrin present in a fibrin sealant mixture can be determined.

EVICEL® Fibrin Sealant (Human), available from Johnson & Johnson Wound Management, Somerville, N.J., is supplied as a kit containing BAC2 (55-85 mg/mL fibrinogen) and thrombin (800-1200 IU/mL human thrombin). BAC2 is a sterile solution, pH 6.7-7.2, which consists mainly of a concentrate of human fibrinogen. The composition of the BAC2 solution is as follows: Concentrate of human fibrinogen (55-85 mg/mL); arginine hydrochloride, glycine, sodium chloride, sodium citrate, calcium chloride, and water for injection.

Thrombin is a sterile solution, pH 6.8-7.2, which contains purified human thrombin. The composition of the Thrombin solution is as follows: Human thrombin (800-1200 IU/mL); calcium chloride, human albumin, mannitol, sodium acetate, and water for injection.

The present inventive method may have other diagnostic and clinical applications to differentiate between fibrinogen and fibrin when the two proteins are together, or to measure the relative amounts of fibrinogen and fibrin in a mixture. In summary, this method is capable of evaluating the conversion of fibrinogen to fibrin, and is applicable to any mixture of fibrinogen/fibrin and thrombin.

Solubilization Step

In one embodiment of the present invention, the samples containing thrombin and fibrinogen/fibrin in dry and/or liquid formulations are solubilized.

The inventive solubilization reagent includes a high concentration of detergent and reducing agent (4% sodium dodecyl sulfate (SDS) and 500 mM dithiothreitol (DTT)), a direct thrombin inhibitor (e.g. 200 mg/mL Pefabloc® SC) in combination with high temperature (95° C.). As a result, thrombin is inactivated and cannot catalyze fibrin generation. Therefore, thrombin and fibrinogen can exist in solubilized form in the same solution without any interaction.

Once solubilized, the proteins are evaluated by electrophoresis and immunoblotting techniques.

Immunoblotting Step

To evaluate the extent of fibrinogen to fibrin conversion, various samples were optionally subjected to SDS-PAGE followed by Western blot analysis or dot blot analysis. A monoclonal antibody [clone 1F7], specific for the fibrinopeptide A of fibrinogen, was used for detection.

Monoclonal Antibody [Clone 1F7] Directed Against Fibrinopeptide A

According to an embodiment of the present invention, the inventive assay utilizes a monoclonal antibody [clone 1F7] directed against fibrinopeptide A (FpA) present on the intact (unreacted) fibrinogen molecule.

The monoclonal antibody was obtained from Abcam Inc. (Cambridge, Mass.) and characterized by electrophoresis and ELISA.

According to an embodiment of the present invention, the presence of FpA is used as an indicator to detect intact fibrinogen. Fibrinogen fully converted to fibrin will not be detected by this antibody due to the absence of FpA.

In a sample containing a mixture of immobilized fibrinogen and fibrin, the antibody will only bind to the immobilized intact fibrinogen.

Test Articles Used for the Inventive Assay

The below description details the composition and preparation of test articles or samples which were utilized in experimental examples demonstrating operation of the inventive assay. The specific test articles or samples are listed in Tables 1 and 2 below.

To evaluate the extent of fibrinogen to fibrin conversion, various samples containing the protein ranging from intact fibrinogen to fibrin (reaction product) as well as control samples were tested by Western blot and direct dot blot detection techniques. A monoclonal antibody specific for fibrinopeptide A of fibrinogen, [clone 1F7], was used for detection.

Starting material used to prepare test articles included commercially available purified fibrinogen, highly concentrated thrombin and fibrinogen components from a commercially available fibrin sealant and also included a fibrinogen-containing pad manufactured by Ethicon, Inc., as described above.

Unreacted samples included purified fibrinogen, the fibrinogen component of fibrin sealant, and biological powder that was extracted from dry a fibrinogen-containing pad. Fully reacted samples included clotted liquid fibrin sealant and powder extracted from a fibrinogen-containing pad which was fully hydrated for clot formation. A partially reacted sample included powder extracted from a fibrinogen-containing pad exposed to a limited volume of aqueous medium.

All samples not containing thrombin were dissolved in an aqueous solution (solubilizing buffer) at 95° C., containing a final concentration of 0.1 M Tris-HCl, 20 mg/mL SDS buffer and 7.7 mg/mL DTT as a reducing agent, to achieve a fibrinogen concentration of approximately 10 mg/mL.

All samples containing thrombin were dissolved in the solubilizing buffer described above which also contained a final concentration of 2 mg/mL of Pefabloc® SC (4-(2-Aminoethyl)benzenesulfonyl fluoride hydrochloride), used here as a thrombin inhibitor, which is commercially available from Fluka, Sigma-Aldrich, (St. Louis, Mo.) to minimize any thrombin activity during sample preparation.

Samples were prepared as follows: The solubilizing buffer was prepared and heated to 95° C. for each sample. The solubilizing buffer was then added into a vial containing dry protein or protein solution to achieve a fibrinogen/fibrin concentration of approximately 10 mg/mL. The resulting mixture was stirred manually and kept at 95° C. until full reduction and solubilization of the proteins were achieved (up to 3 hours).

Purified fibrinogen sample (≥95% clottable fibrinogen) was obtained from Enzyme Research Laboratories (South Bend, Ind.) and was dissolved in the solubilizing buffer (as described above) to achieve a fibrinogen concentration of approximately 10 mg/mL.

The fibrinogen component of EVICEL® (BAC2) fibrin sealant was utilized for some tests. The concentration of fibrinogen was 55-85 mg/mL and other proteins and excipients are also included in the formation including fibronectin, albumin, arginine hydrochloride, glycine, sodium chloride, and sodium citrate.

Additionally, the thrombin component of EVICEL® fibrin sealant was used for some tests. The activity of the thrombin was 800-1200 IU/mL and the formulation also contained calcium chloride, human albumin, mannitol, and sodium acetate.

For sample preparation, fibrinogen component of fibrin sealant was dissolved at 95° C. in a solubilizing buffer at a final concentration of 0.1 M Tris-HCl, 20 mg/mL SDS buffer and 7.7 mg/mL DTT, to achieve a fibrinogen concentration of approximately 10 mg/mL.

A fibrin sealant clot sample was prepared by simultaneously mixing equal volumes of EVICEL® fibrinogen and thrombin components into a test tube and incubating the sample at physiologically optimal temperature (e.g. 37° C.) for up to 2 hours to ensure full fibrin clot formation. The fully clotted mixture was then dissolved in the solubilizing buffer to achieve a fibrinogen/fibrin concentration of approximately 10 mg/mL, as described above.

The lyophilized protein powder was extracted from dry fibrinogen-containing pad samples by agitating the fibrinogen and thrombin coated fabric in solvent (methyl perfluoropropyl ether), followed by evaporation of the solvent. A portion of this powder was hydrated in aqueous medium (200 mM tris-HCl, 150 mM NaCl, pH 7.4) and incubated at physiologically optimal temperature (e.g. 37° C.) for up to 2 hours to ensure full fibrin clot formation. The resulting clot was then dissolved in the solubilizing buffer to achieve a fibrinogen/fibrin concentration of approximately 10 mg/mL, as described above.

Fibrinogen-containing pad samples, exposed to specified temperature and humidity conditions of 25° C./60% RH, were prepared as follows: fibrinogen-containing pad samples were positioned in an environmental chamber set to conditions of 25° C./60% RH for either 1 hour or 24 hours. The fibrinogen-containing pad samples were then optionally vacuum-dried and their powder extracted, as described above. The powder extract was then dissolved in the solubilizing buffer to achieve a concentration of approximately 10 mg/mL fibrinogen, as described above.

Fibrinogen-containing pad samples were also partially clotted by hydration in a limited volume of aqueous medium (200 mM tris-HCl, 150 mM NaCl, pH 7.4) to allow for fibrin clot formation and then optionally vacuum dried. The powder was then extracted and then dissolved in the solubilizing buffer to achieve a fibrinogen/fibrin concentration of approximately 10 mg/mL, as described above.

Test article "Sample treatment buffer" contained only solubilizing buffer, as described above.

EXAMPLE 1

Western Blot Immunoassay

The samples tested are enumerated in Table 1. After solubilization to approximately 10 mg/mL fibrinogen/fibrin concentration, the samples were further diluted in solubilization buffer to optimize sample protein concentrations for SDS-PAGE. Samples were then loaded onto a 4-12% SDS-polyacrylamide gel at final fibrinogen/fibrin amounts shown in Table 1. Proteins were then subjected to gel electrophoresis using standard laboratory techniques. SDS-PAGE was run at 125 volts until the dye-front reached the foot of the gel. After electrophoresis, the proteins were transferred onto a protein-binding membrane (e.g. nitrocellulose) using standard laboratory techniques.

After transfer, the membrane was incubated in blocking solution (e.g. casein and/or detergent containing solution, as known in the art) to prevent non-specific binding. The nitrocellulose membrane was then rinsed and incubated at ambient temperature in a monoclonal antibody (primary antibody, [clone 1F7]) solution with specific affinity to the fibrinopeptide A portion of human fibrinogen.

The membrane was washed with antibody wash buffer (e.g. saline solution containing detergent, as known in the art) to remove any unbound antibody and then incubated in a secondary antibody solution (commercially available goat anti-mouse IgG, conjugated to alkaline phosphatase) and washed again with antibody wash buffer to remove any unbound antibody.

The banding pattern was visualized by incubation of the nitrocellulose membrane in a commercially available substrate for alkaline phosphatase.

Figure 3:
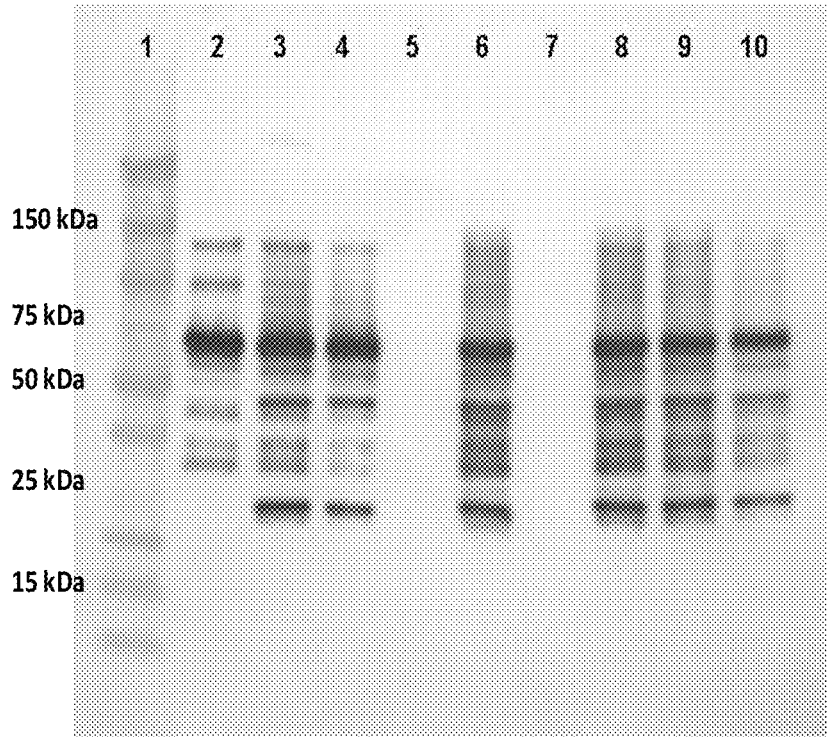
FIG. 3 shows image of the nitrocellulose membrane after performing the Western blot assay.

Referring now to FIG. 3, an image of the nitrocellulose membrane after performing the Western blot procedure is presented. Table 1 presents the lane assignments for Western blot for tested samples and also the test results with the interpretation of the banding patterns.

TABLE 1

Western Blot Test Sample Loading Information and Results

| Lane | Sample Description | Amount of Fibrinogen/Fibrin Loaded (µg) | Interpretation of Results |
|---|---|---|---|
| 1 | Molecular Weight Marker | N/A | N/A |
| 2 | Purified Fibrinogen | 1.25 | Fibrinogen detected in the purified fibrinogen sample |
| 3 | Fibrinogen-containing component of fibrin sealant | 1.25 | Fibrinogen detected in fibrinogen-containing component of fibrin sealant sample |
| 4 | Fibrinogen-containing component of fibrin sealant | 0.63 | Fibrinogen detected in fibrinogen-containing component of fibrin sealant sample |
| 5 | Clotted fibrin sealant | 0.50 | No fibrinogen detected in the clotted fibrin sealant sample |
| 6 | Powder extracted from dry fibrinogen-containing pad | 2.13 | Fibrinogen detected in powder extracted from dry fibrinogen-containing pad sample |
| 7 | Hydrated powder extracted from a fibrinogen-containing pad | 2.13 | No fibrinogen detected in the hydrated powder extracted from a fibrinogen-containing pad sample |
| 8 | Powder extracted from a fibrinogen-containing pad after 1-hour humidification | 2.13 | Fibrinogen detected in powder extracted from a fibrinogen-containing pad after 1-hour humidification sample |
| 9 | Powder extracted from a fibrinogen-containing pad after 24-hour humidification | 2.13 | Fibrinogen detected in powder extracted from a fibrinogen-containing pad after 24-hour humidification sample |
| 10 | Powder extracted from partially clotted fibrinogen-containing pad | 2.13 | An intermediate level of fibrinogen (relatively fainter banding pattern) detected in powder extracted from a pad sample exposed to a limited volume of aqueous medium |

FIG. 3 and Table 1 indicate that fibrinogen was successfully detected in samples containing non-clotted fibrinogen samples, i.e. fibrinogen was detected in purified fibrinogen (Lane 2), fibrinogen-containing component of commercially available fibrin sealant (Lanes 3, 4), and dry and humidified fibrinogen-containing pad powder extracts (Lane 6, 8, 9). No fibrinogen was detected in fully clotted samples i.e. in clotted fibrin sealant sample (Lane 5) and hydrated powder extracted from a fibrinogen-containing pad (Lane 7). An intermediate level of fibrinogen (reflected by relatively fainter banding pattern) was detected in powder extracted from the fibrinogen-containing pad samples exposed to a limited volume of aqueous medium (Lane 10). No discernible difference in banding patterns was observed between dry and humidified (25° C./60% RH, up to 24 hours) fibrinogen-containing pad powder extracts, indicating that the fibrinogen-containing pad was not subject to any appreciable fibrinogen to fibrin conversion under these conditions.

Figure 4:
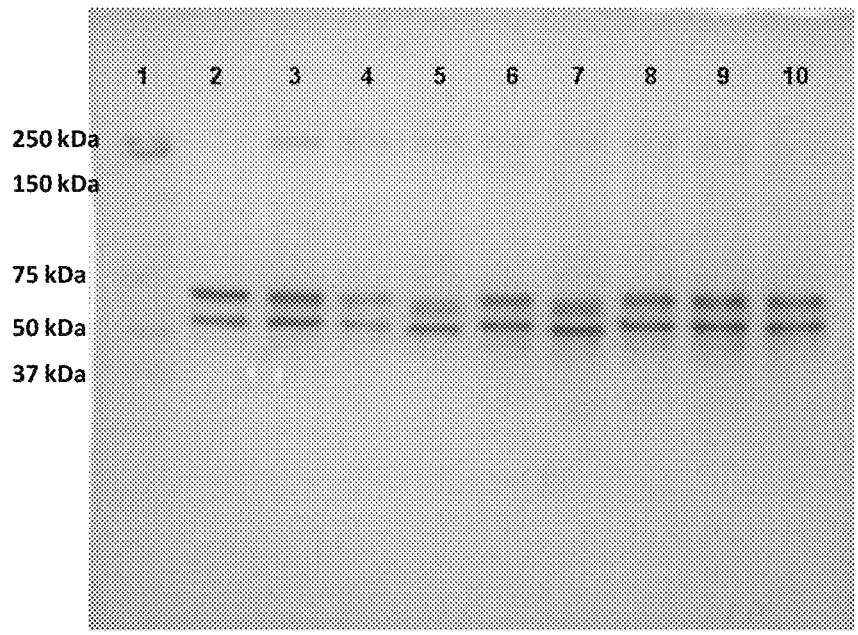
FIG. 4 shows an image of the gel stained with Coomassie blue immediately after protein transfer from gel to nitrocellulose membrane.

After the transfer of proteins from the gel to the nitrocellulose membrane, the gel was stained with Coomassie blue using standard laboratory techniques to confirm that protein was present in all of the lanes. An image of the gel is shown in FIG. 4 indicating protein was detected in all lanes. In lanes where no fibrinogen was detected on the Western blot, i.e. in the clotted fibrin Sealant (Lane 5) and powder extracted from a fibrinogen-containing pad which was fully hydrated (Lane 7), α-chain and β-chain of fibrinogen were present. In lanes where fibrinogen was detected on the Western blot, i.e. in purified fibrinogen (Lane 2), fibrinogen-containing component of fibrin sealant (Lanes 3, 4), and powder extracted from a fibrinogen-containing pad (Lane 6, 8, 9), Aα-chain and Bβ-chain of fibrinogen were present.

EXAMPLE 2

Dot Blot Immunoassay

A rapid fibrinogen assay was developed utilizing a dot blot immunoassay procedure. The gel electrophoresis step of the above Western blot procedure is omitted, with the approach based on large proteins in the sample being adsorbed onto the membrane, while small molecules like FpA washed away prior to treatment with the anti-FpA antibody. A similar immunoblotting procedure was then followed as described below.

The samples tested are enumerated in Table 2. A 1.5 cm×1.5 cm array of squares was drawn on nitrocellulose protein-binding membrane. After solubilization, a suitable volume (e.g. 2 µL) of sample or control material was applied to the center of each square. The sample or control were allowed to completely dry on the membrane. The nitrocellulose membrane was then incubated in blocking solution to prevent non-specific binding.

The membrane was rinsed and then incubated in a monoclonal antibody (primary antibody, [clone 1F7]) solution with specific affinity to the fibrinopeptide A portion of human fibrinogen at ambient temperature (same as in Western blot procedure described above), and then washed with buffer to remove any unbound antibody. The membrane was incubated in secondary antibody solution for 1 hour (same as in as in Western blot procedure), and then washed with buffer to remove any unbound antibody. The membrane was incubated with commercially available substrate for alkaline phosphatase (same as in Western blot procedure) until the dot intensities were suitably developed for visualization (e.g. 5-30 minutes), the membrane was then rinsed to stop the reaction.

The size and intensity of the stained area was then quantified by optical densitometry and the relationship with fibrinogen concentration was assessed.

Figure 5:
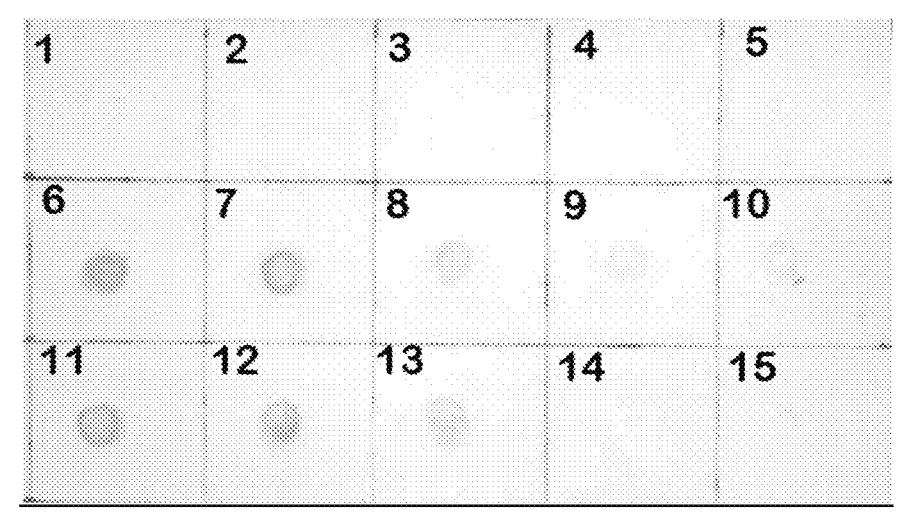

Referring now to FIG. 5, an image of the nitrocellulose membrane after performing the dot blot procedure is presented, with the numbers corresponding to sample numbers, as enumerated in Table 2. Table 2 presents the sample descriptions, quantity of fibrinogen/fibrin protein loaded, optical density of the stained areas on the membrane as measured by densitometry and the results of the test interpreting the observed patterns. The optical density is expressed by a number on a grayscale ranging from 0 corresponding to complete black (high fibrinogen content) to 255 corresponding to white (absence of fibrinogen).

TABLE 2

Dot Blot Test Sample Loading Information and Results

| Sample/Control | Amount Fibrinogen/ Fibrin Loaded (µg) | Optical Density | Detection Results |
|---|---|---|---|
| 1. Sample treatment buffer | 0 | 223 | No staining observed with sample buffer |
| 2. Blank | N/A | 232 | No staining observed with the blank |
| 3. Hydrated powder extracted from a fibrinogen-containing pad | 0.850 | 238 | No fibrinogen detected in the fully wetted and clotted fibrinogen-containing pad powder extract |
| 4. Hydrated powder extracted from a fibrinogen-containing pad | 0.425 | 236 | No fibrinogen detected in the extract from the fibrinogen-containing pad which was fully wetted and clotted |
| 5. Hydrated powder extracted from a fibrinogen-containing pad | 0.213 | 230 | No fibrinogen detected in the extract from the fibrinogen-containing pad which was fully wetted and clotted |
| 6. Dry fibrinogen-containing pad powder extract | 0.850 | 178 | Fibrinogen detected |
| 7. Dry fibrinogen-containing pad powder extract | 0.425 | 193 | Fibrinogen detected |
| 8. Dry fibrinogen-containing pad powder extract | 0.213 | 222 | Fibrinogen detected |
| 9. Dry fibrinogen-containing pad powder extract | 0.106 | 231 | Fibrinogen detected |
| 10. Dry fibrinogen-containing pad powder extract | 0.053 | 224 | Fibrinogen detected |
| 11. Powder extracted from a fibrinogen-containing pad after 1-hour humidification | 0.425 | 185 | Fibrinogen detected |
| 12. Powder extracted from a fibrinogen-containing pad after 24-hour humidification | 0.425 | 192 | Fibrinogen detected |
| 13. Powder extracted from partially clotted fibrinogen-containing pad samples | 0.425 | 217 | Fibrinogen detected |
| 14. Powder extracted from fully clotted fibrinogen-containing pad samples | 0.425 | 233 | No fibrinogen detected when the fibrinogen-containing pad was fully clotted |
| 15. Blank (empty) | N/A | 226 | No staining was observed with the blank |

Figure 6:
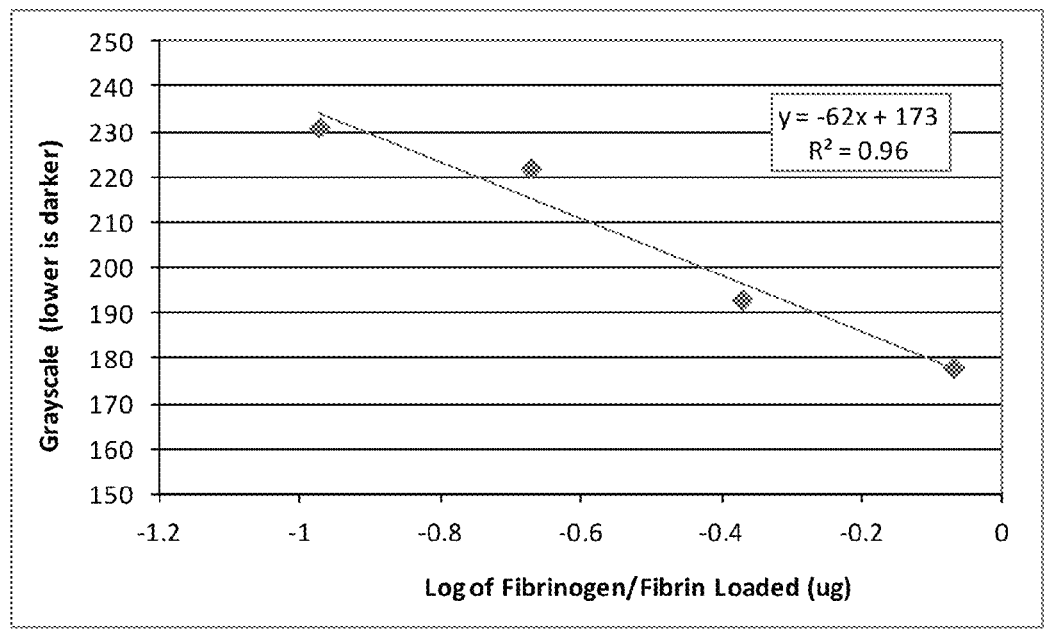
FIG. 6 shows a graph indicating a linear relationship between fibrinogen concentrations and staining intensity.

Referring now to FIG. 6, a graph is presented showing a relationship between fibrinogen concentrations and staining intensity. The grayscale optical density values on the dot blot membrane were plotted as a function of the log of the concentration of the protein (fibrinogen) in the sample. The analysis was performed with samples 6-9 as listed in Table 2, with the fibrinogen/fibrin loading ranging from 0.850 to 0.106 µg. The intensity of fibrinogen staining was proportional to the amount of fibrinogen present in sample ($r^2=0.96$).

Analysis of data presented in FIGS. 5-6 and Table 2 indicates that the intensity of fibrinogen staining was proportional to the amount of intact fibrinogen present in the sample. No discernible staining was observed with sample buffer or with the blank (empty) (samples 1, 2 and 15) and no fibrinogen was detected in hydrated powder extracted from the fibrinogen-containing pad, which was prepared by fully hydrating the biological powder (samples 3-5) or when the entire fibrinogen-containing pad was fully clotted (sample 14). Fibrinogen was detected in dry fibrinogen-containing pad powder extracts (samples 6-10) and in fibrinogen-containing pad samples exposed to humidity for 1 hr (sample 11) or 24 hr (sample 12), and in the powder extracted from partially clotted fibrinogen-containing pad samples (sample 13).

Block-Diagram of the Process

Figure 7:
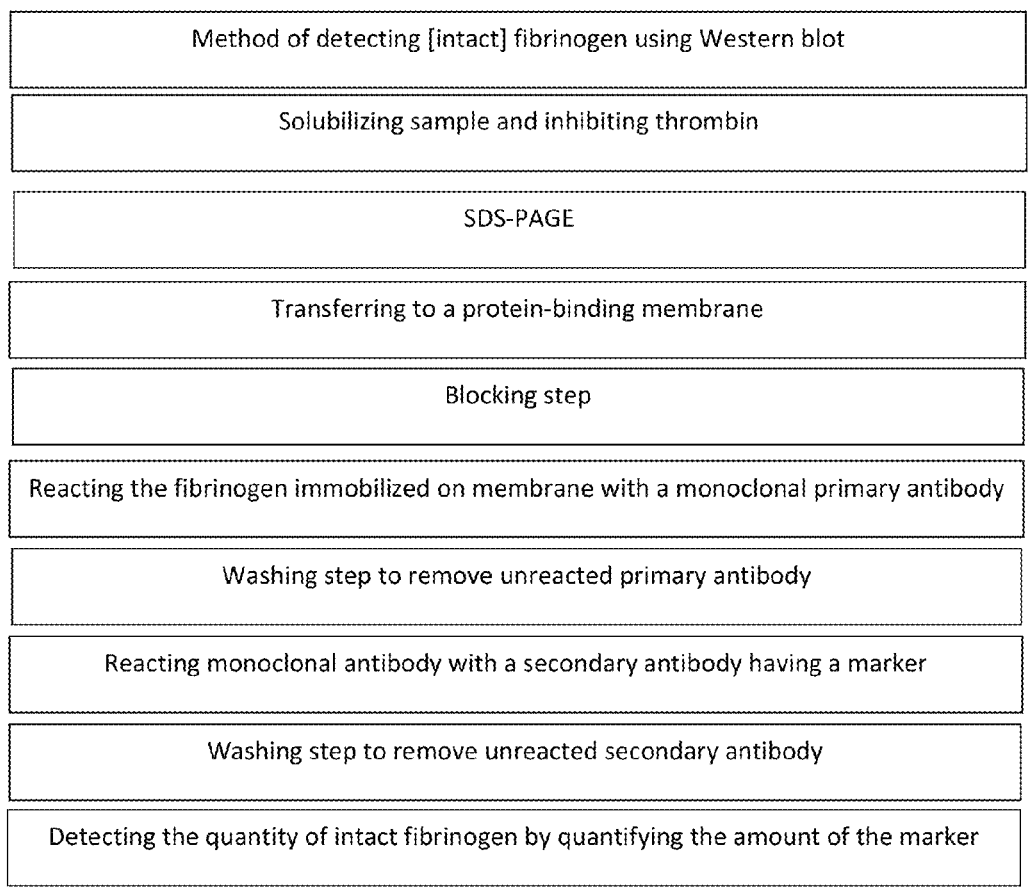
FIG. 7 shows block-diagram of the inventive method for the Western blot assay.
Figure 8:
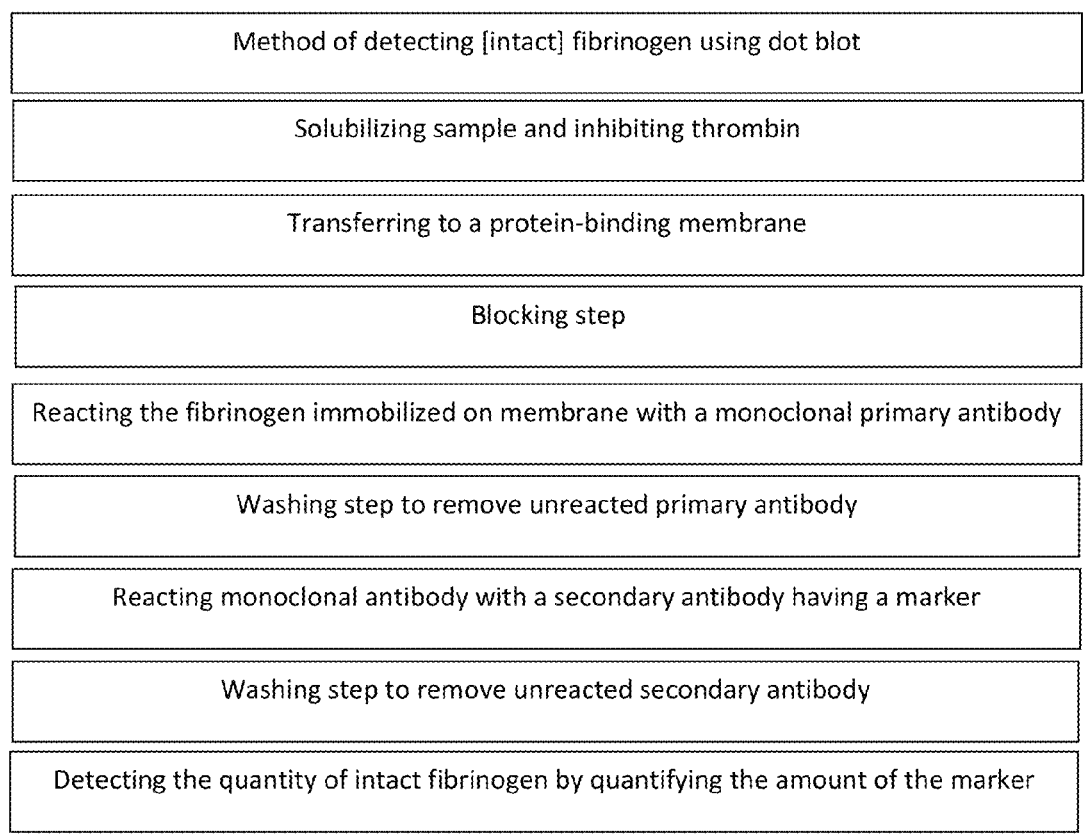
FIG. 8 shows block-diagram of the inventive method for the dot blot assay.

Referring now to FIGS. 7 and 8, block-diagrams of the inventive method are presented for Western blot and dot blot, respectively.

According to one embodiment of the present invention, a method of detecting intact fibrinogen using Western blot comprises the steps of a) solubilizing sample and inhibiting thrombin; b) performing SDS-PAGE; c) transferring sample onto a protein-binding membrane; d) blocking step; e) reacting the fibrinogen immobilized on membrane with a monoclonal primary antibody; f) washing step to remove unbound primary antibody; g) reacting monoclonal antibody with a secondary antibody having a marker; h) washing step to remove unreacted unbound secondary antibody and i) detecting the quantity of intact fibrinogen by quantifying the amount of the marker.

According to another embodiment of the present invention, a method of detecting intact fibrinogen using dot blot comprises the steps of a) solubilizing sample and inhibiting thrombin; b) applying sample onto a protein-binding membrane; c) blocking step; d) reacting the fibrinogen immobilized on membrane with a monoclonal primary antibody; e) washing step to remove unbound primary antibody; f) reacting monoclonal antibody with a secondary antibody having a marker; g) washing step to remove unbound secondary antibody; and h) detecting the quantity of intact fibrinogen by quantifying the amount of the marker.

While the above examples demonstrate certain embodiments of the invention, they are not to be interpreted as limiting the scope of the invention, but rather as contributing to a complete description of the invention.

We claim:

1. A method of detecting intact fibrinogen, comprising the steps of:
   a) Providing a sample containing at least some fibrinogen optionally converted at least in part to fibrin, and optionally containing thrombin;
   b) Solubilizing the sample in a solubilizing solution that inhibits thrombin activity;
   c) Applying a portion of said sample to a protein-binding membrane and immobilizing the fibrinogen on said membrane;
   d) Subjecting said membrane to at least one blocking step and removing fibrinopeptide A cleaved from fibrinogen from said membrane;
   e) Reacting the fibrinogen immobilized on said membrane with a primary monoclonal antibody capable of binding to fibrinopeptide A moiety to form a fibrinogen-antibody complex;
   f) Subjecting said membrane to at least one washing step to remove any unbound primary monoclonal antibody;
   g) Reacting said monoclonal antibody that formed the fibrinogen-antibody complex with a secondary antibody having a marker;
   h) Subjecting said membrane to at least one washing step to remove any unbound secondary antibody having a marker; and
   i) Detecting the quantity of intact fibrinogen in the sample by quantifying the amount of the marker.

2. The method of claim 1, wherein said sample contains an unknown amount of intact fibrinogen.

3. The method of claim 1, wherein said sample is solid, liquid, or semi-liquid.

4. The method of claim 1, wherein said sample contains lyophilized fibrinogen and thrombin.

5. The method of claim 1, wherein said primary monoclonal antibody capable of binding to fibrinopeptide A moiety is clone 1F7.

6. The method of claim 1, wherein said primary monoclonal antibody is capable of binding to fibrinopeptide B moiety on the fibrinogen.

7. The method of claim 1, wherein said secondary antibody having a marker is goat anti-mouse IgG, conjugated to alkaline phosphatase.

8. The method of claim 1, wherein said step of detecting the quantity of intact fibrinogen in the sample is determined by incubating the protein-binding membrane with a substrate for alkaline phosphatase.

9. The method of claim 1, wherein said marker is an electrochemically detectable marker, a colorimetrically detectable marker, radiologically detectable marker, magnetically detectable marker or a fluorescent marker.

* * * * *